US012383906B2

United States Patent
Yager et al.

(10) Patent No.: US 12,383,906 B2
(45) Date of Patent: Aug. 12, 2025

(54) DEVICE AND METHOD FOR DETECTION OF PATHOGENS

(71) Applicant: University of Washington, Seattle, WA (US)

(72) Inventors: Paul Yager, Seattle, WA (US); Steven Bennett, Seattle, WA (US); Erin K. Heiniger, Seattle, WA (US); Sujatha Kumar, Seattle, WA (US); Kamal Girish Shah, Seattle, WA (US)

(73) Assignee: University of Washington, Seattle, WA (US)

( * ) Notice: Subject to any disclaimer, the term of this patent is extended or adjusted under 35 U.S.C. 154(b) by 665 days.

(21) Appl. No.: 17/838,807

(22) Filed: Jun. 13, 2022

(65) Prior Publication Data

US 2022/0395838 A1     Dec. 15, 2022

Related U.S. Application Data

(60) Provisional application No. 63/210,459, filed on Jun. 14, 2021.

(51) Int. Cl.
| | | |
|---|---|---|
| *B01L 7/00* | (2006.01) | |
| *B01L 3/00* | (2006.01) | |
| *C12Q 1/6806* | (2018.01) | |

(52) U.S. Cl.
CPC ........... *B01L 7/52* (2013.01); *B01L 3/502715* (2013.01); *C12Q 1/6806* (2013.01);
(Continued)

(58) Field of Classification Search
CPC .. B01L 7/52; B01L 3/502715; B01L 2200/10; B01L 2300/0861;
(Continued)

(56) References Cited

U.S. PATENT DOCUMENTS

| | | |
|---|---|---|
| 7,464,811 B2 | 12/2008 | Patterson et al. |
| 8,652,782 B2 | 2/2014 | Fischer et al. |
| (Continued) | | |

FOREIGN PATENT DOCUMENTS

| | | |
|---|---|---|
| CA | 2991918 A1 | 1/2016 |
| EP | 3400284 A1 | 11/2018 |
| (Continued) | | |

OTHER PUBLICATIONS

Augustine, R. et al., "Loop-Mediated Isothermal Amplification (LAMP): A Rapid, Sensitive, Specific, and Cost-Effective Point-of-Care Test for Coronaviruses in the Context of COVID-19 Pandemic," Biology 2020, 9, 182, 1-17.

(Continued)

*Primary Examiner* — Lessanework Seifu
(74) *Attorney, Agent, or Firm* — Christensen O'Connor Johnson Kindness PLLC

(57) ABSTRACT

Fluidic devices, systems, and methods for analyzing an analyte are described. In an embodiment, the fluidic devices include a housing defining a lysis chamber shaped to receive a biological sample; a lysis buffer storage chamber disposed within the housing and carrying a lysis buffer configured to lyse cells of the biological sample; a cap configured to cooperatively couple to the housing; a compressor configured to compress the lysis buffer storage chamber and expel the lysis buffer from the lysis buffer storage chamber and into the lysis chamber when the cap is uncoupled from the housing; and a porous membrane in selective fluidic communication with the lysis chamber.

20 Claims, 21 Drawing Sheets

(52) U.S. Cl.
CPC ... *B01L 2200/10* (2013.01); *B01L 2300/0861* (2013.01); *B01L 2300/1805* (2013.01); *B01L 2400/0457* (2013.01)

(58) Field of Classification Search
CPC ..... B01L 2300/1805; B01L 2400/0457; B01L 2200/16; B01L 3/5023; B01L 2300/0672; B01L 2400/0677; B01L 3/5029; C12Q 1/6806
See application file for complete search history.

(56) References Cited

U.S. PATENT DOCUMENTS

| | | |
|---|---|---|
| 8,889,424 B2 | 11/2014 | Ehrenkranz et al. |
| 9,075,042 B2 | 7/2015 | Cook et al. |
| 2019/0210778 A1 | 7/2019 | Muir et al. |

FOREIGN PATENT DOCUMENTS

| | | |
|---|---|---|
| JP | 2015516583 A | 6/2015 |
| WO | 2017/117666 A1 | 7/2017 |
| WO | 2017214315 A1 | 12/2017 |

OTHER PUBLICATIONS

Wang, S. et al., "A lab-on-chip device for the sample-in-result-out detection of viable Salmonella using loop-mediated isothermal amplification and real-time turbidity monitoring," Royal Society of Chemistry; Lab Chip, 2020, 20, 2296-2305.

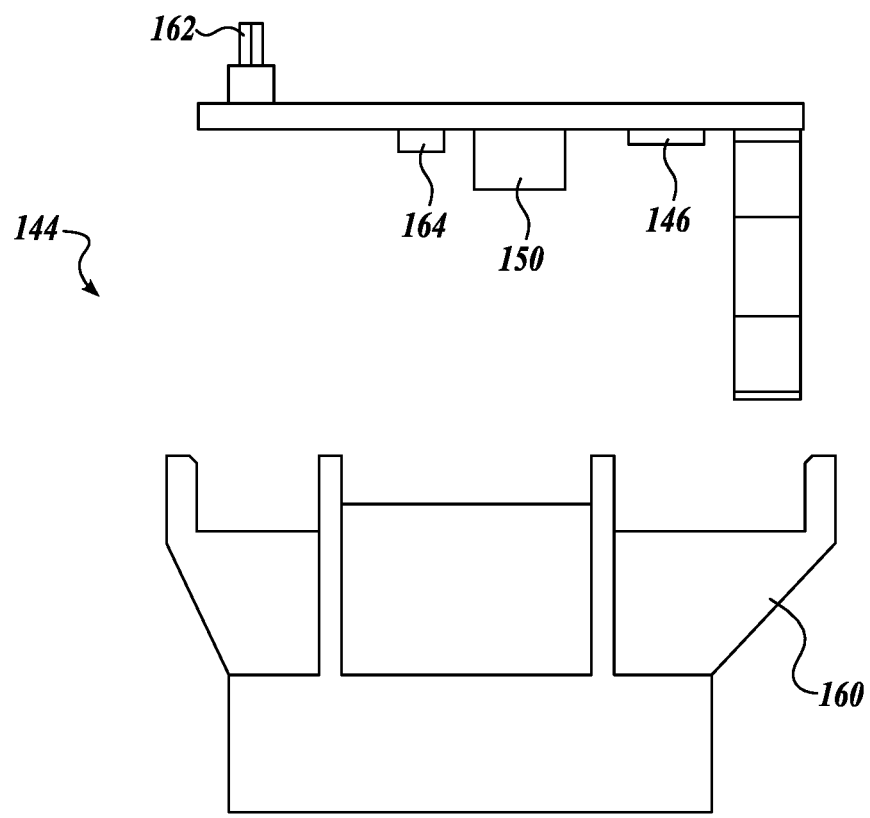
FIG. IJ

DEVICE AND METHOD FOR DETECTION OF PATHOGENS

CROSS-REFERENCE TO RELATED APPLICATION

This application claims the benefit of U.S. Provisional Application No. 63/210,459 filed Jun. 14, 2021, the entire disclosure of which is hereby incorporated by reference.

BACKGROUND

There is presently a need to identify individuals and families in need of treatment for infectious diseases and isolation without moving people, thereby risking unnecessary spreading of pathogens. In particular, there is a need to access a large fraction of the population for surveillance of existing and novel pathogens. To do so, a low-cost tool that is simple enough to be usable by untrained individuals and provides laboratory-quality would be preferable, particularly, where results can be transmitted automatically (by Bluetooth or other methods) to an operator's cell phone, and thence to the entity that provided that phone to the user, and thence to doctors, hospitals and the infectious disease authorities.

SUMMARY

In certain aspects, the present disclosure provides fluidic devices and diagnostic systems to address these and relates challenges.

In an aspect, the present disclosure provides a fluidic device comprising: a housing defining a lysis chamber shaped to receive a biological sample; a lysis buffer storage chamber disposed within the housing and carrying a lysis buffer configured to lyse cells of the biological sample; a cap configured to cooperatively coupled to the housing; a compressor configured to compress the lysis buffer storage chamber and expel the lysis buffer from the lysis buffer storage chamber and into the lysis chamber when the cap is uncoupled from the housing; and a porous membrane in selective fluidic communication with the lysis chamber.

In another aspect, the present disclosure provides a diagnostic system comprising: a fluidic device comprising: a housing defining a lysis chamber shaped to receive a biological sample; a lysis buffer storage chamber disposed within the housing and carrying a lysis buffer configured to lyse cells of the biological sample; a cap configured to cooperatively coupled to the housing; a closure sensor configured to generate a closure signal when the cap is cooperatively coupled with the housing; a compressor configured to compress the lysis buffer storage chamber and expel the lysis buffer from the lysis buffer storage chamber and into the lysis chamber when the cap is uncoupled from the housing; and a porous membrane in selective fluidic communication with the lysis chamber; and a controller in operative communication with the fluidic device including logic that, when executed by the controller, cause the diagnostic system to perform operations including: heating the lysis chamber in response to the closure signal. This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1J is another partial exploded view of the fluidic device of FIG. 1A, in accordance with an embodiment of the present disclosure;

DETAILED DESCRIPTION

Embodiments of a fluidic device, a system, a method for of an analyte are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In an aspect, the present disclosure provides a fluidic device for detecting a target in a biological sample. In an embodiment, the fluidic device comprises a housing defining a lysis chamber shaped to receive a biological sample; a lysis buffer storage chamber disposed within the housing and carrying a lysis buffer configured to lyse cells of the biological sample; a cap configured to cooperatively coupled to the housing; a compressor configured to compress the lysis buffer storage chamber and expel the lysis buffer from the lysis buffer storage chamber and into the lysis chamber when the cap is uncoupled from the housing; and a porous membrane in selective fluidic communication with the lysis chamber.

In this regard, attention is directed to FIGS. 1A-1J in which a fluidic device 100 according to an embodiment of the present disclosure is illustrated.

Figure 1A:
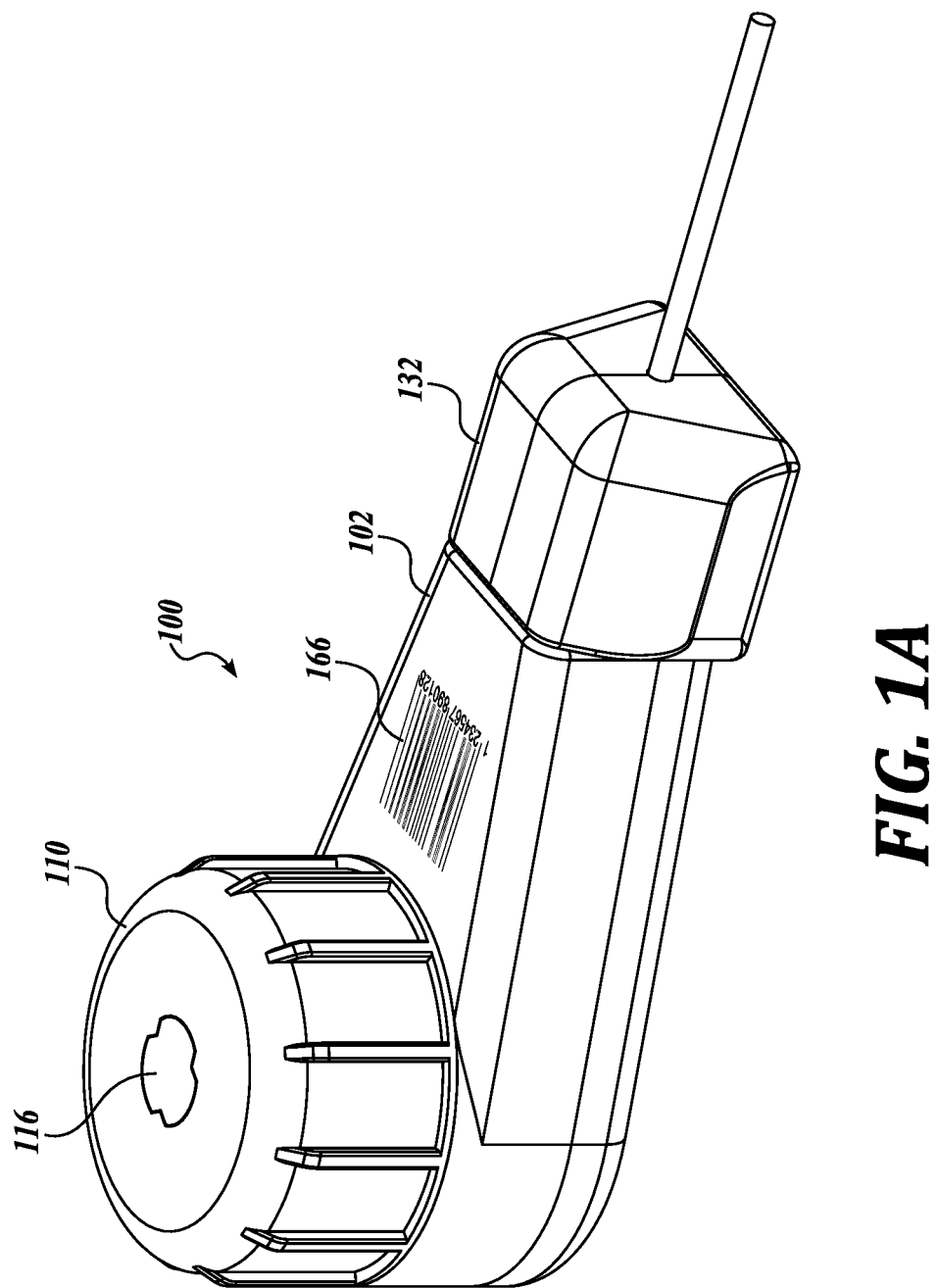
FIG. 1A is a perspective illustration of a fluidic device, in accordance with an embodiment of the disclosure.
Figure 1B:
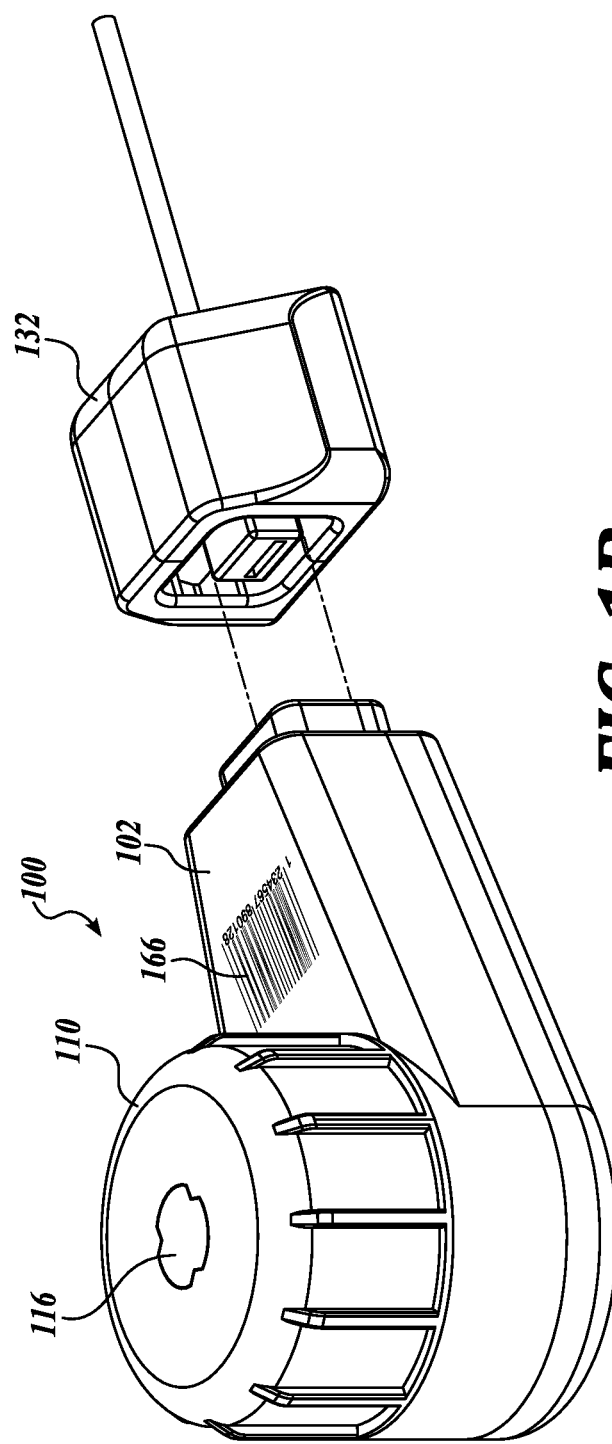
FIG. 1B is another perspective illustration of the fluidic device of FIG. 1A.
Figure 1C:
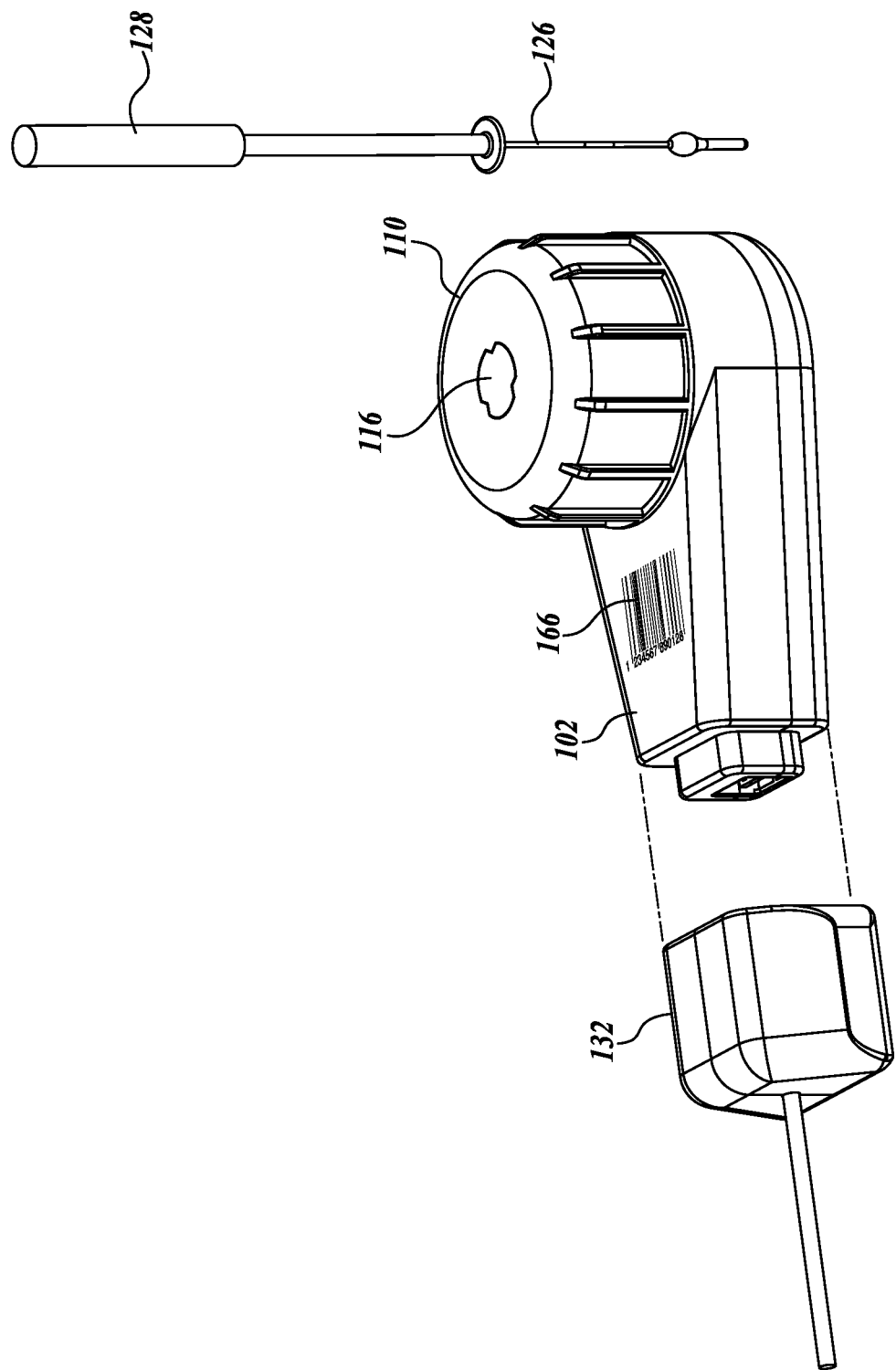
FIG. 1C is another perspective illustration of the fluidic device of FIG. 1A.
Figure 1D:
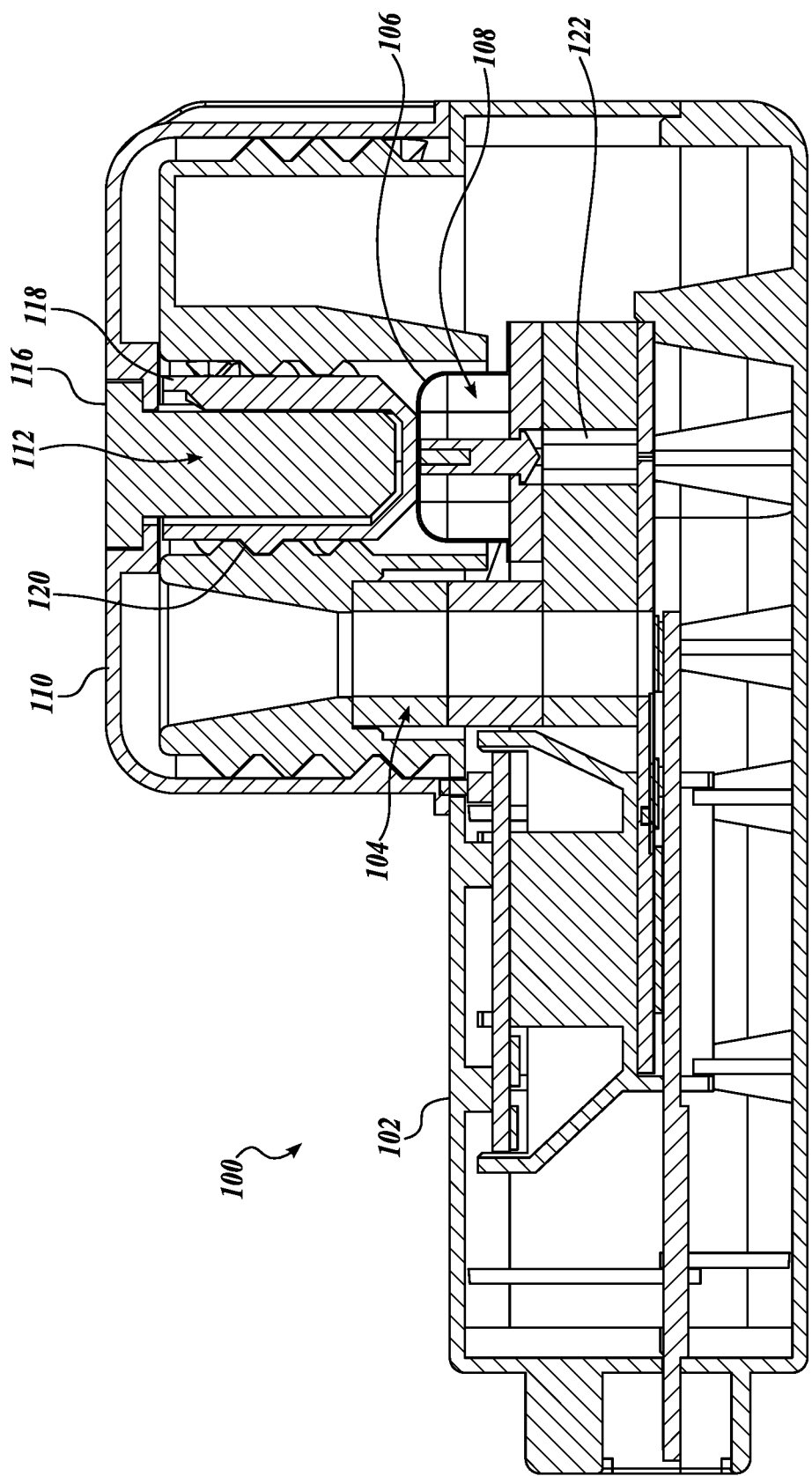
FIG. 1D is a cross-section view of the fluidic device of FIG. 1A in a closed configuration, in accordance with an embodiment of the disclosure.
Figure 1E:
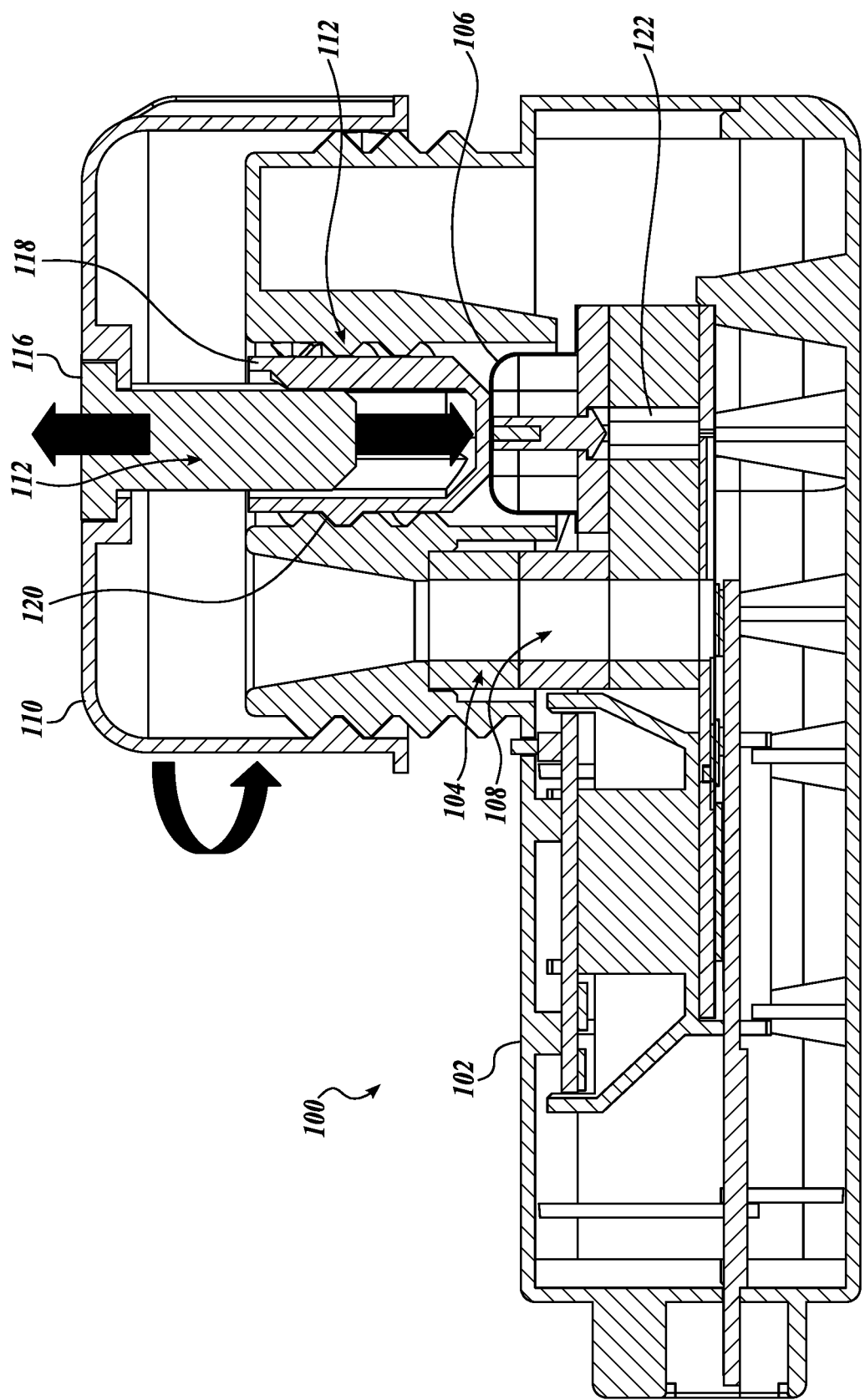
FIG. 1E is a cross-section view of the fluidic device of FIG. 1D in an open configuration, in accordance with an embodiment of the present disclosure.
Figure 1F:
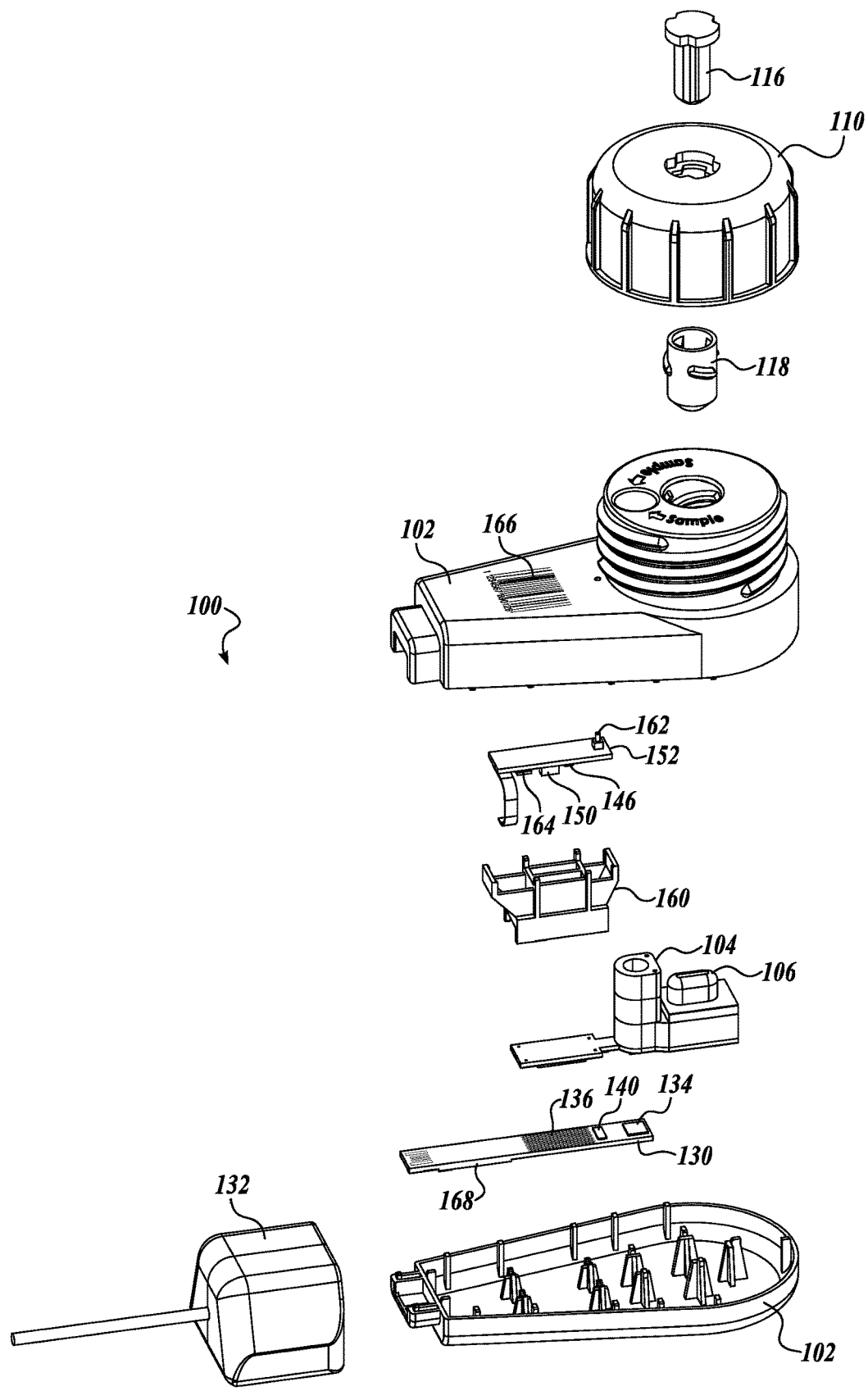
FIG. 1F is an exploded view of the fluidic device of FIG. 1A, in accordance with an embodiment of the present disclosure.
Figure 1G:
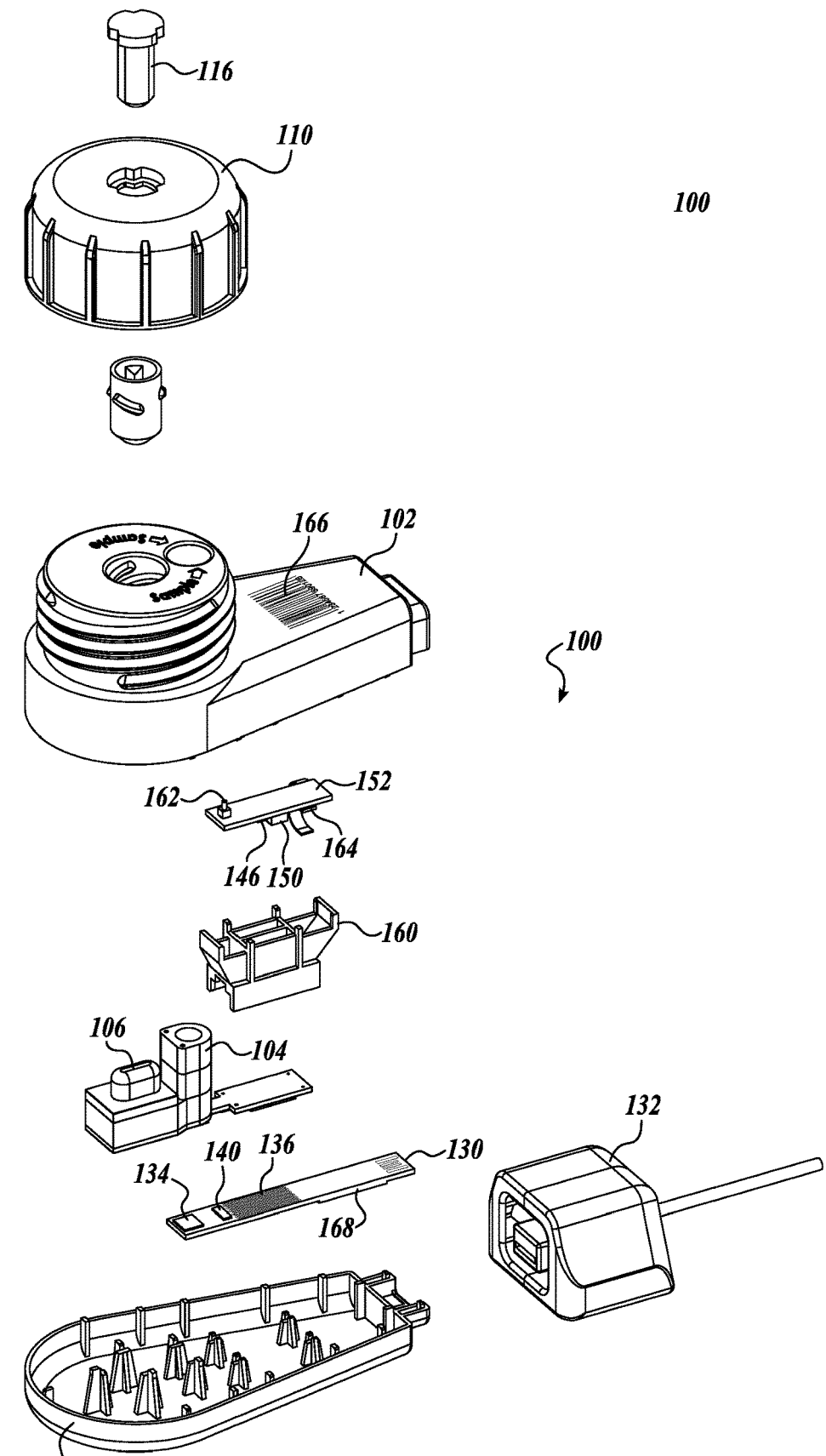
FIG. 1G is another exploded view of the fluidic device of FIG. 1A, in accordance with an embodiment of the present disclosure.
Figure 1H:
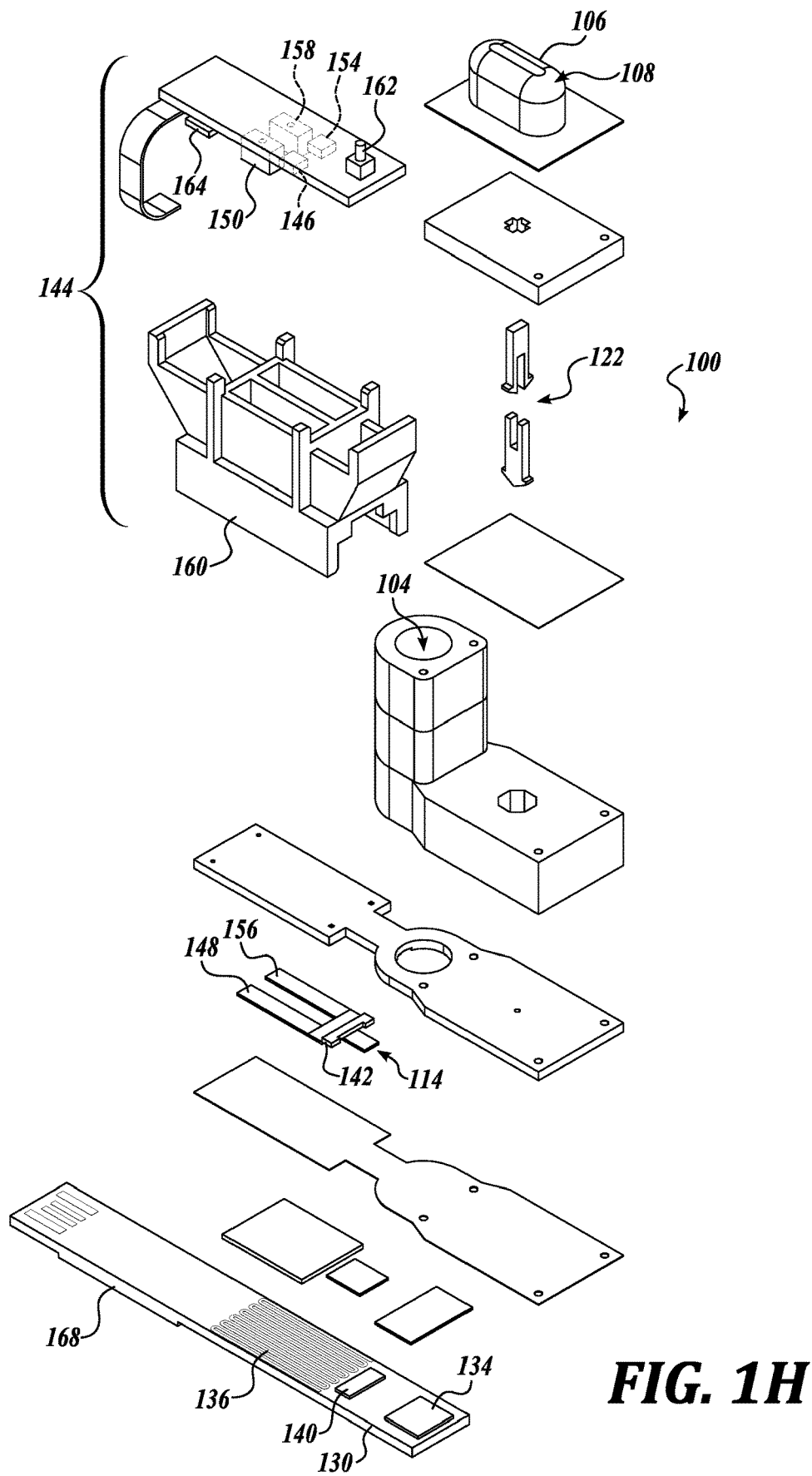
FIG. 1H is a partial exploded view of the fluidic device of FIG. 1A, in accordance with an embodiment of the present disclosure.
Figure 1I:
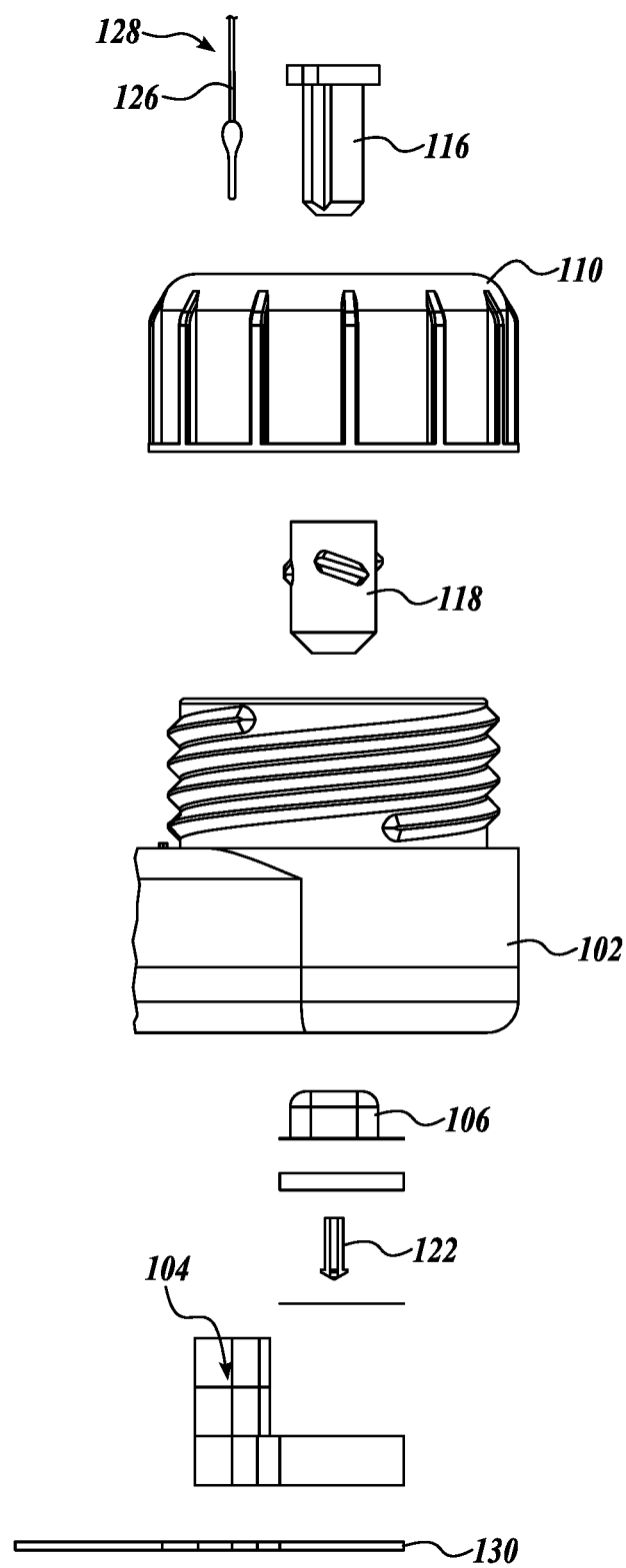
FIG. 1I is another partial exploded view of the fluidic device of FIG. 1A, in accordance with an embodiment of the present disclosure.

FIG. 1A is a perspective illustration of the fluidic device 100. FIG. 1B is another perspective illustration of the fluidic device 100. FIG. 1C is another perspective illustration of the fluidic device 100. FIG. 1D is a cross-section view of the fluidic device 100. FIG. 1E is a cross-section view of the fluidic device 100 in an open configuration. FIG. 1F is an exploded view of the fluidic device 100. FIG. 1G is another exploded view of the fluidic device 100. FIG. 1H is a partial exploded view of the fluidic device 100. FIG. 1I is another partial exploded view of the fluidic device 100. FIG. 1J is another partial exploded view of the fluidic device 100.

In the illustrated embodiment, the fluidic device 100 is shown to include a housing 102 defining a lysis chamber 104 shaped to receive a biological sample, such as a liquid sample; a lysis buffer storage chamber 106 disposed within the housing 102 and carrying a lysis buffer 108 configured to lyse cells of the biological sample; a cap 110 configured to cooperatively couple to the housing 102; a compressor 112 configured to compress the lysis buffer storage chamber 106 and expel the lysis buffer 108 from the lysis buffer storage chamber 106 and into the lysis chamber 104 when the cap 110 is uncoupled from the housing 102; and a porous membrane 114 in selective fluidic communication with the lysis chamber 104.

In an embodiment, compressor 112 comprises a compressor actuator 116 coupled to the cap 110; and a compressor member 118 shaped to couple with the compressor actuator 116 and cooperatively engage with threads 120 defined by the housing 102 to depress the lysis buffer storage chamber 106 when the cap 110 is rotated to uncouple the cap 110 from the housing 102. See, for example, FIGS. 1D and 1E. In the illustrated embodiment, the fluidic device 100 is shown to further include a piercing member 122 shaped and positioned to pierce the lysis buffer storage chamber 106 upon actuation of the compressor 112 to place the lysis buffer storage chamber 106 in fluidic communication with the lysis chamber 104. See, for example, FIG. 1I. In an embodiment, the piercing member 122 is a lance or needle shaped to pierce or otherwise puncture the lysis buffer storage chamber 106 when applied thereto.

As shown, the fluidic device 100 includes a biological sample retrieval device, such as a sample swab 128, including a stem 126 configured to be received by the lysis chamber 104.

In the illustrated embodiment, the fluidic device 100 is shown to also include a closure sensor 162 configured to generate a closure signal when the cap 110 is cooperatively coupled with the housing 102, discussed further herein with respect to FIGS. 2A-2H.

In an embodiment, the fluidic device 100 includes a fluidics printed circuit board 130 configured to receive electrical power from a power source 132. As shown in FIGS. 1A and 1B, the housing 102 and the fluidics circuit board a coupleable to the power source 132, such as to receive power therefrom. In an embodiment, the fluidics printed circuit board 130 comprising a lysis heater 134 configured to receive electrical power from the power source 132 and positioned to heat the lysis chamber 104, such as to aid in lysing a sample disposed therein.

In the illustrated embodiment, the fluidics printed circuit board 130 further comprises an amplification heater 136 configured to receive electrical power from the power source 132 and positioned to heat an amplification zone of the porous membrane 114. Such amplification zone heating may be configured to heat reagents and samples in the amplification zone, thereby assisting in an amplification reaction, such as a nucleic acid amplification reaction.

As shown, the fluidics printed circuit board 130 further comprises a valve heater 140 configured to receive electrical power from the power source 132 and positioned to heat a phase-change valve 142 of the porous membrane 114 configured to selectively place the lysis chamber 104 in fluidic communication with the amplification zone. In an embodiment, as the phase-change valve 142 is heated, such as to change a phase of at least a portion of the phase-change valve 142, the lysis chamber 104 is thereby placed in fluidic communication with the porous membrane 114.

In an embodiment, the fluidic device 100 is configured to perform one or more optical detection assays, such as one or more optical detection assays of an analyte or an amplicon of the analyte, on the porous membrane 114. In this regard, in an embodiment, the fluidic device 100 is shown to include an optoelectronics module 144. In the illustrated embodiment, the optoelectronics module 144 is shown to include a light source 146 positioned to illuminate a detection zone 148 of the porous membrane 114; a photodetector 150 positioned to receive fluorescence emitted from the detection zone 148 and generate a fluorescence signal based upon the received fluorescence. See, for example, FIGS. 1F, 1G, 1H, and 1J. In an embodiment, the light source 146 is configured to optically excite one or more reagents disposed on the porous membrane 114, such as when the one or more reagents are coupled to an analyte or an amplicon thereof.

As shown, the housing 102 further comprises a light control housing 160 shaped and positioned to optically isolate the light source 146 and the photodetector 150 from the second light source 154 and the second photodetector. In an embodiment, the light control housing 160 is configured to shield light from an outside environment of the fluidic device 100 from entering the light control housing 160. In this regard, the light control housing 160 prevents exterior light (i.e., light other than from the light source 146 or the second light source 154) from illuminating the porous membrane 114 including the detection zone 148 and the control detection zone 156.

In an embodiment, the light source 146 and the photodetector 150 are disposed on an optoelectronics printed circuit board 152 in operative communication with the fluidics printed circuit board 130, such as to receive power therefrom as may be provided by the power source 132.

In an embodiment, the fluidic device 100 is configured to perform one or more control assays, such as to confirm receipt of a sample. In this regard, in an embodiment, the optoelectronics module 144 further comprises a second light source 154 positioned to illuminate a control detection zone 156 of the porous membrane 114; and a second photodetector 158 positioned to receive control fluorescence emitted from the control detection zone 156 of the porous membrane 114 and generate a signal based on the received control fluorescence. In an embodiment, the control detection zone 156 includes one or more control reagents configured to detect the presence or absence of one or more control analytes, such as a human epithelial gene, or amplicons thereof, such as may be used to confirm that a viable sample was obtained and transmitted to the porous membrane 114.

Figure 5:
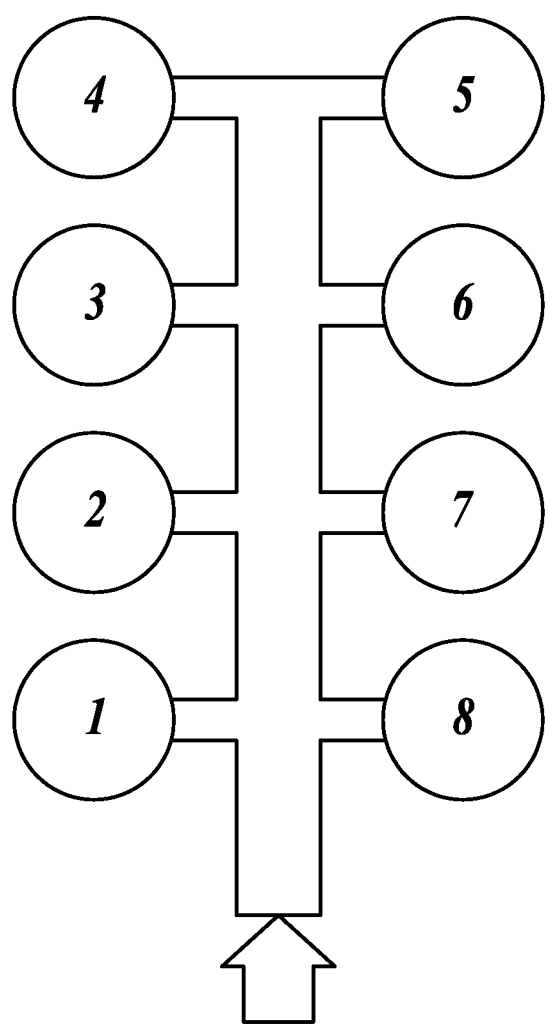
FIG. 5 is a schematic illustration of a porous membrane including multiplexed detection zones, in accordance with an embodiment of the disclosure.

In an embodiment, the porous membrane 114 is configured to perform a number of detection reactions, such as on a number of fluidically isolated legs of the porous membrane 114, such as illustrated in FIG. 5 in legs 1-8.

Figure 6:
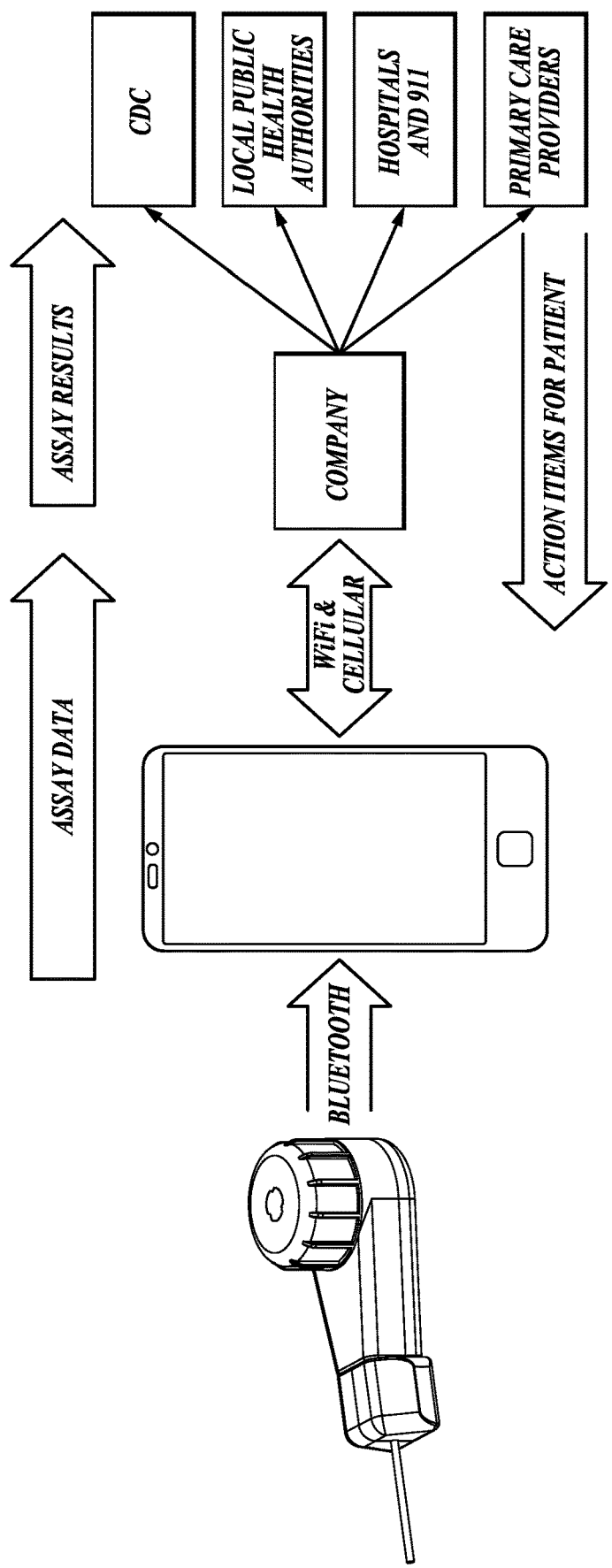
FIG. 6 schematically illustrates connectivity of a fluidics system, in accordance with an embodiment of the disclosure.

Referring back to FIGS. 1A-1J, in the illustrated embodiment, the fluidic device 100 includes a transmitter 164 configured to transmit the fluorescence signal. As shown in FIG. 6, the fluidic device according to embodiments of the present disclosure is configured to communicate with and transmit signals to a variety of other devices and/or systems. Referring still to FIG. 6, the fluidic device is shown in operative communication with a smartphone, such as through a Bluetooth connection, and, thereby, in WiFi or cellular connection with a variety of other devices, systems, and organizations, such as to receive signals from the fluidic device indicative of a presence or absence of an analyte assayed by the fluidic device. In an embodiment, the fluidic device of FIG. 6 is an example of fluidic device 100.

Referring back to FIGS. 1A-1J, in an embodiment, the fluidic device 100 includes a controller 168 in operative communication with various fluidic device 100 components, such as to choreograph their operation. In an embodiment, the controller 168 is operatively coupled to fluidic device 100 components by one or more of a wired connection or a wireless connection. In some embodiments, the wireless connection is a direct wireless connection, such as a Bluetooth connection, a near field communication (NFC) connection, a direct WiFi connection, or any other direct wireless connection. In some embodiments, the wireless connection is an indirect connection via one or more wireless networks, such as a cellular network (e.g., 4G, LTE), a WiFi network, a local area network, any other network, or any combination thereof. In some embodiments, the wireless connection permits the controller 168 to be located remotely from other fluidic device 100 components.

In an embodiment, the controller 168 includes a processor and non-transitory computer-readable storage medium. In an embodiment, the non-transitory computer-readable storage medium has stored thereon computer-readable program instructions that, upon execution by a processor, cause the processor to perform one or more operations, as discussed further herein.

In an embodiment, the controller 168 is in operative communication with the fluidic device 100 including logic that, when executed by the controller 168, cause the fluidic device 100 to perform operations including heating the lysis chamber 104 in response to the closure signal.

In an embodiment, the controller 168 is configured to place the lysis chamber 104 in fluidic communication with the porous member. In this regard, in an embodiment, the controller 168 further includes logic that, when executed by the controller 168, causes the fluidic device 100 to perform operations including heating a phase-change valve 142 of the porous membrane 114 to place the lysis chamber 104 in fluidic communication with an amplification zone of the porous membrane 114.

In an embodiment, the fluidic device 100, such as through operations controlled by the controller 168, is configured to aid in an amplification reaction, such as a nucleic acid amplification reaction in the porous membrane 114. In this regard, in an embodiment, the controller 168 further includes logic that, when executed by the controller 168, causes the fluidic device 100 to perform operations including heating the amplification zone, such as for a time and to a temperature suitable to perform a nucleic acid amplification reaction.

As discussed further herein, in an embodiment, the fluidic device 100 further comprises an optoelectronics module 144, such as an optoelectronics module 144 comprising a light source 146 positioned to illuminate a detection zone 148 of the porous membrane 114; and a photodetector 150 positioned to receive fluorescence emitted from the detection zone 148 and generate a fluorescence signal based upon the received fluorescence. In such an embodiment, the controller 168 may further include logic that, when executed by the controller 168, causes the fluidic device 100 to perform operations including generating a diagnosis signal based upon the fluorescence signal. In an embodiment, the controller 168 further includes logic that, when executed by the controller 168, causes the fluidic device 100 to perform operations including transmitting the fluorescence signal, such as to one or more devices or systems separate and distinct from the fluidic device 100 but in operative communication therewith.

In an embodiment, the fluidic device 100 includes an identifier 166, such as a QR code, disposed on the housing 102 or packaging associated with the fluidic device 100. In an embodiment, that QR code will trigger download of the app appropriate to the phone in use at the time, and that is specific to the test type and lot. In an embodiment, the app will start by showing the end-user a short video of the proper use of the fluidic device 100, and will require the user to state whether the tested person is to be the tester them self (in which case the patient ID information and GPS location will be taken from the phone directly) of another person whose ID they must enter manually (or scan) before proceeding with the test. In an embodiment, the next step is to plug in the fluidic device 100 and establish a connection with the device via Bluetooth or other methods, which could include optical or acoustic communication, or direct communication via a wire, which can be confirmed by the App. Out-of-date tests or ones with electronic device failures can be confirmed at this point. At the end of the test the user will be given the chance to opt in to sending their test data to various stakeholders.

In certain embodiment, the fluidic device of the present disclosure includes a closure sensor configured to generate a closure signal when the cap is cooperatively coupled with the housing. In that regard, attention is directed to FIGS. 2A-2H in which a fluidic device 200 according to an embodiment of the present disclosure is illustrated.

Figure 2B:
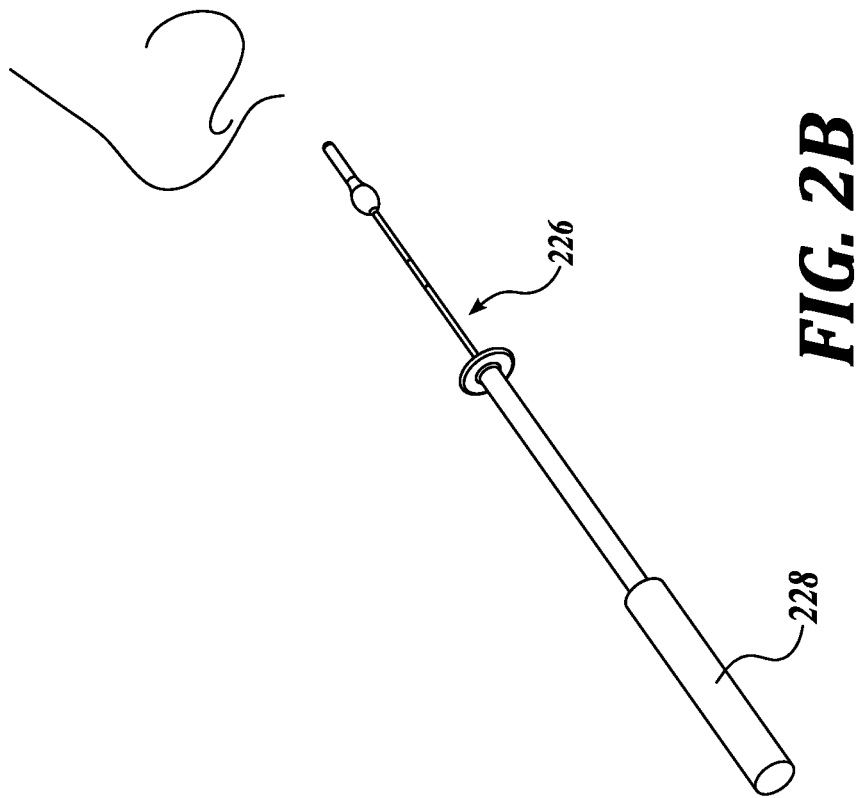
FIGS. 2A and 2B illustrate obtaining a biological sample with a sample swab, in accordance with an embodiment of the disclosure.
Figure 2A:
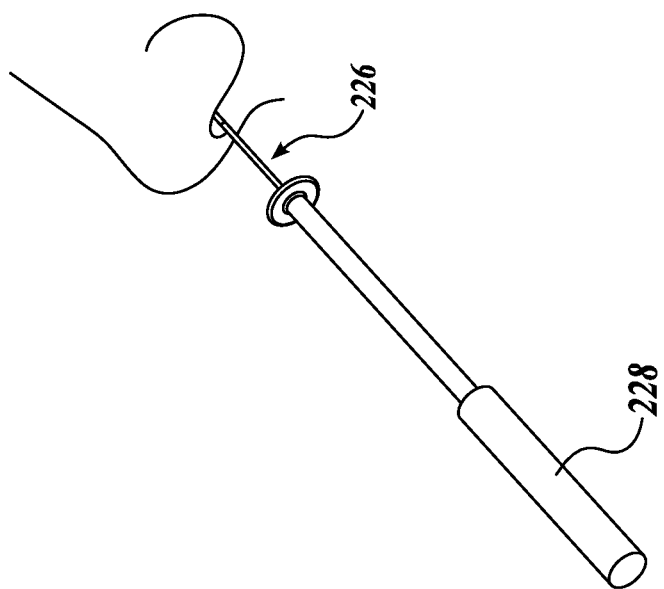

FIGS. 2A and 2B illustrate obtaining a biological sample with a sample swab 228. As shown, the sample swab 228 is shown to include a stem 226 shaped to be received by the lysis chamber 204, such as through the cap 210.

Figure 2C:
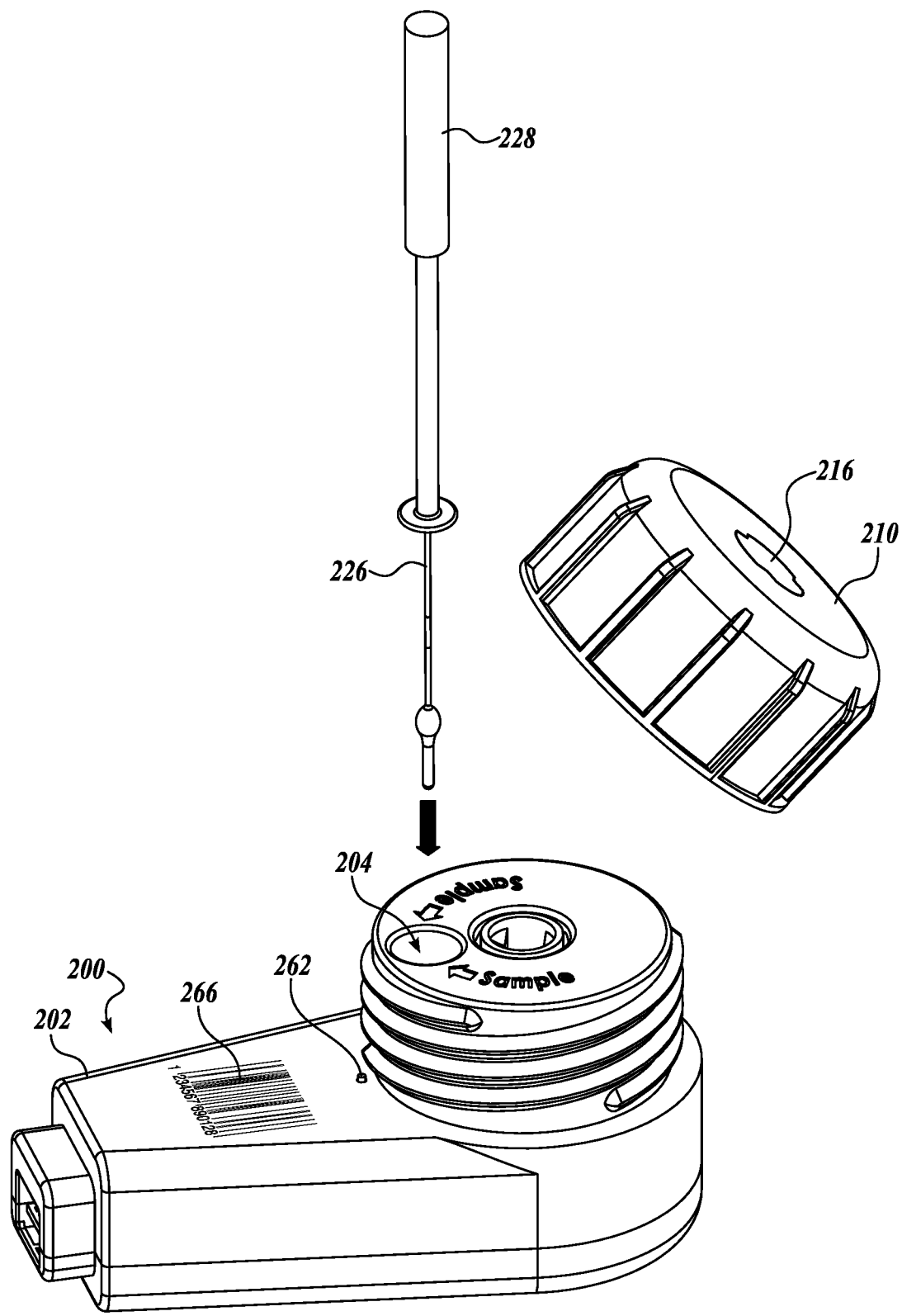
FIG. 2C illustrates inserting the sample swab of FIGS. 2A and 2B into a fluidic device according to an embodiment of the present disclosure.

FIG. 2C illustrates inserting the sample swab 228 of FIGS. 2A and 2B into the fluidic device 200. In the illustrated embodiment, the fluidic device 200 is shown to include a housing 202 defining a lysis chamber 204 shaped to receive a biological sample; a lysis buffer storage chamber 206 disposed within the housing 202 and carrying a lysis buffer configured to lyse cells of the biological sample; a cap 210 configured to cooperatively coupled to the housing 202; a compressor 212 configured to compress the lysis buffer storage chamber 206 and expel the lysis buffer from the lysis buffer storage chamber 206 and into the lysis chamber 204 when the cap 210 is uncoupled from the housing 202; and a porous membrane (not shown, see, for example, FIG. 1H) in selective fluidic communication with the lysis chamber 204.

Figure 2D:
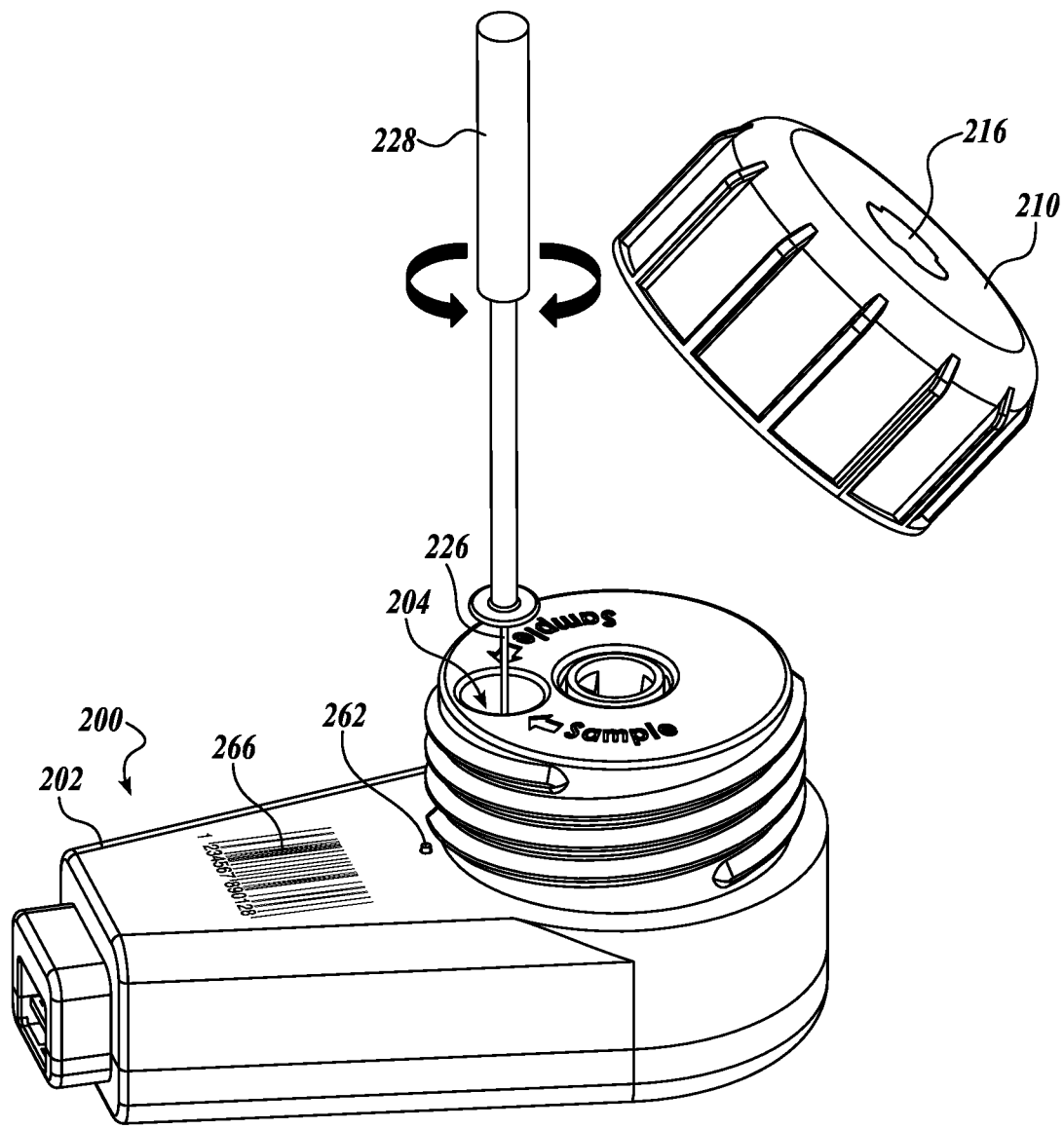
FIG. 2D illustrates rotating the sample swab in the fluidic device of FIG. 2C, in accordance with an embodiment of the present disclosure.
Figure 2E:
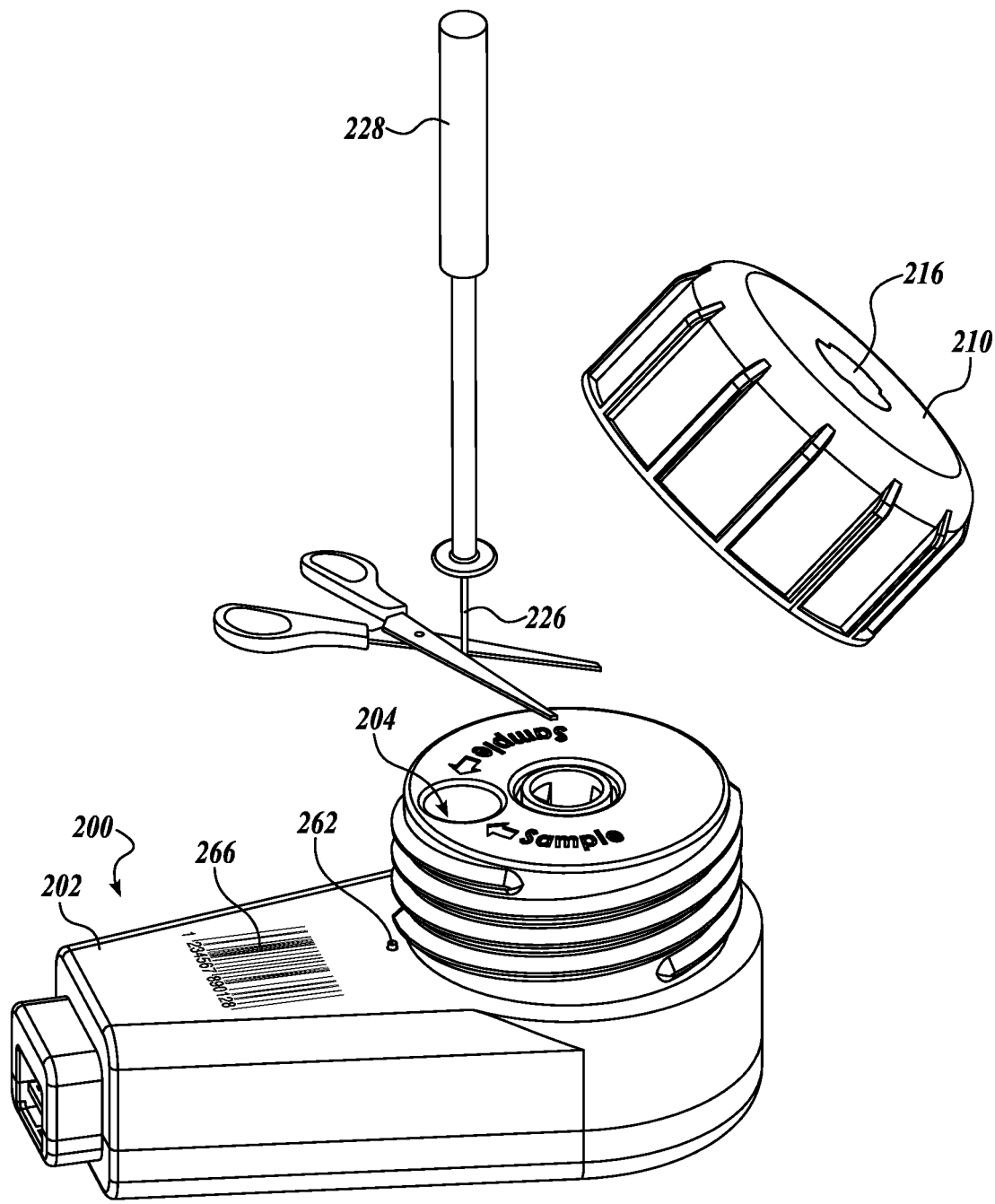
FIG. 2E illustrates removing a stem of the sample swab from the sample swab of FIGS. 2A and 2B, in accordance with an embodiment of the present disclosure.
Figure 2F:
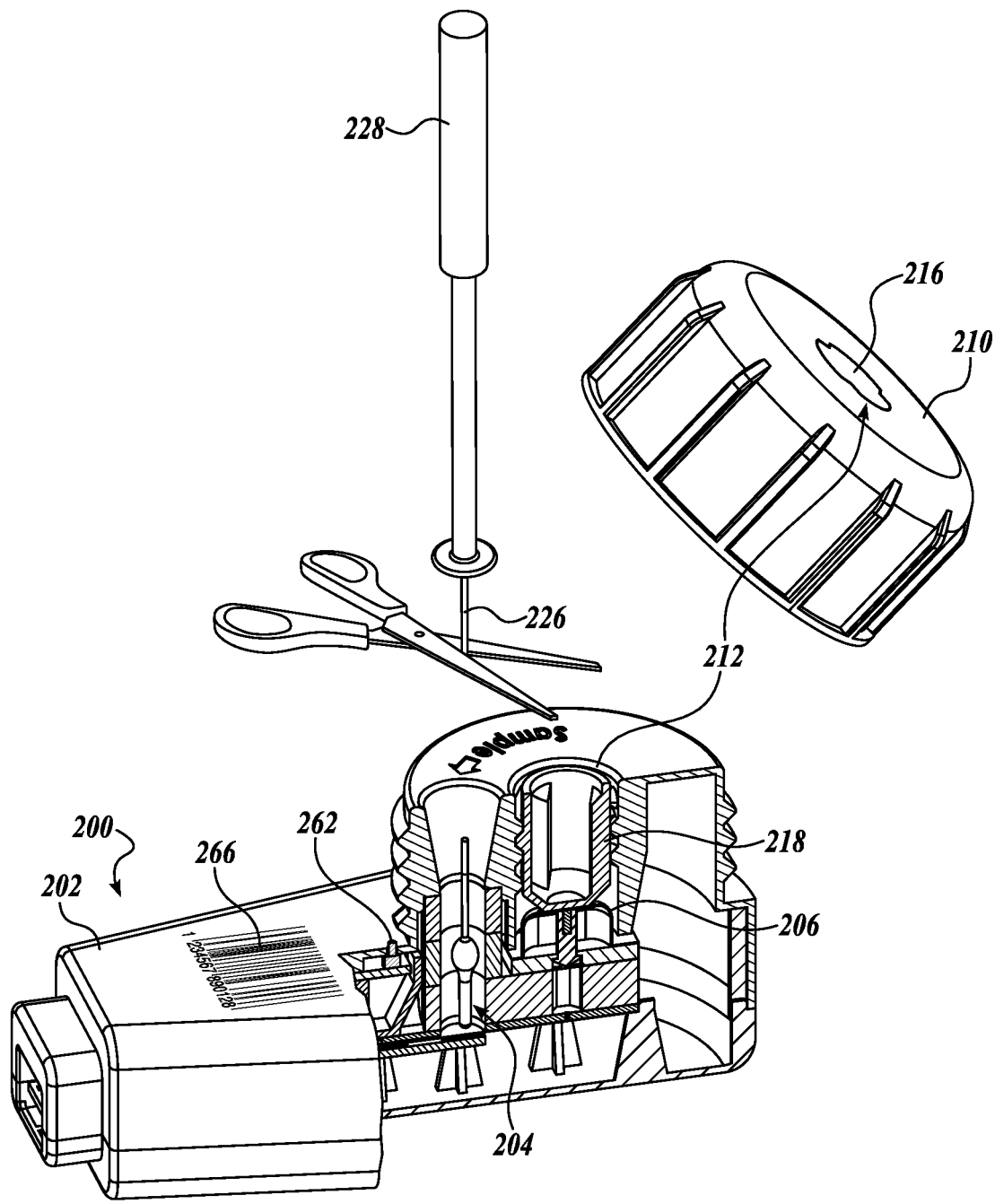
FIG. 2F is a partial cutaway of the fluidic device of FIG. 2E showing a portion of the sample swab disposed in the fluidic device, in accordance with an embodiment of the present disclosure.

FIG. 2D illustrates rotating the sample swab 228 in the fluidic device 200 such as the transfer the sample into the lysis chamber 204. FIG. 2E illustrates removing a stem 226 of the sample swab 228 from the sample swab 228, shown here being removed with a pair of scissors, thereby placing a portion of the sample swab 228 including the stem 226 into the lysis chamber 204. FIG. 2F is a partial cutaway of the fluidic device 200 of FIG. 2E showing a portion of the sample swab 228 disposed in the fluidic device 200. As shown, the fluidic device 200 includes a compressor 212, including a compressor actuator 216 and a compressor member 218, as discussed further herein with respect to FIGS. 1A-1J.

Figure 2H:
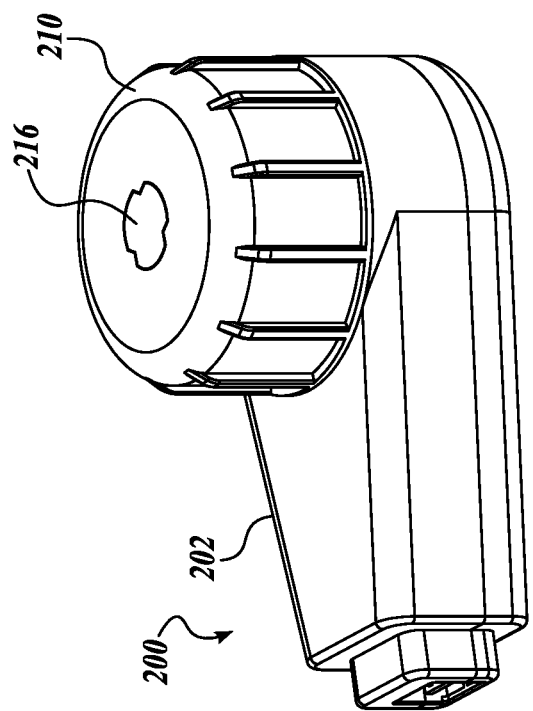
FIG. 2H illustrates coupling a cap of the fluidic device of FIG. 2G to a housing of the fluidic device, thereby actuating the closure sensor, in accordance with an embodiment of the present disclosure.
Figure 2G:
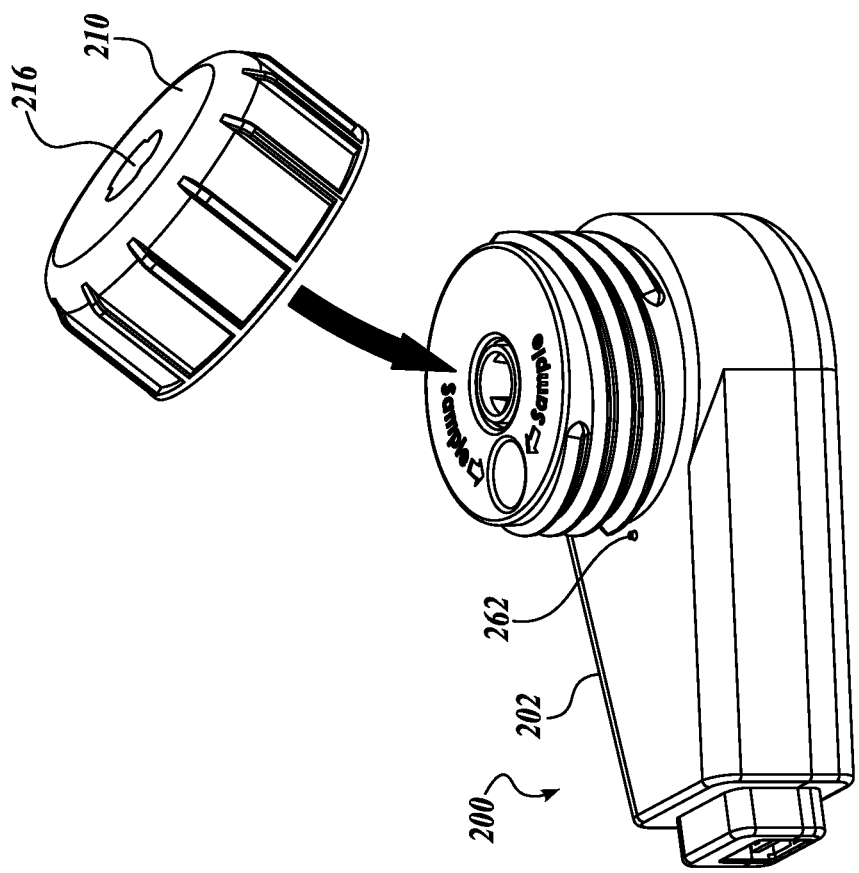
FIG. 2G is a perspective view of the fluidic device of FIG. 2A showing a closure sensor, in accordance with an embodiment of the present disclosure.

FIG. 2G is a perspective view of the fluidic device 200 of FIG. 2A showing the closure sensor 262. In the illustrated embodiment, the closure sensor 262 is shown disposed protruding from the housing 202. As shown further herein in, for example, FIG. 1H, the closure sensor 262 may be coupled to an optoelectronics printed circuit board and, thereby, be operatively coupled to a controller.

FIG. 2H illustrates coupling a cap 210 of the fluidic device 200 of FIG. 2G to a housing 202 of the fluidic device 200, thereby actuating the closure sensor 262. By actuating the closure sensor 262, a signal may be sent to the controller, which thereby activates or starts other operations of the fluidic device 200, such as heating various components to the fluidic device 200 to perform an analyte detection and/or amplification assay.

In an embodiment, the fluidic devices of the present disclosure include a bracket, such as a bracket disposed in the housing of the fluidic device, shaped to couple with a stem of a sample swab, and wherein the cap is shaped to shear the stem as the cap is coupled to the housing when the sample swab is received by the lysis chamber and the stem is coupled to the bracket. In this regard, attention is directed to FIGS. 3A-3E in which a fluidic device 300 according to an embodiment of the present disclosure is illustrated.

Figure 3A:
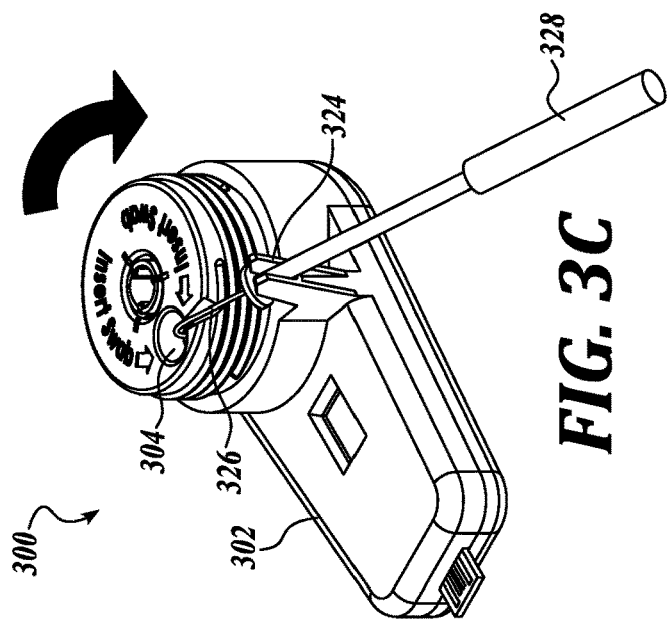
FIG. 3A illustrates a fluidic device in accordance with an embodiment of the present disclosure.

FIG. 3A illustrates a fluidic device 300. As shown, the fluidic device 300 includes a housing 302 defining a lysis chamber 304 shaped to receive a biological sample; and a cap 310 configured to cooperatively coupled to the housing 302. In an embodiment, the fluidic device 300 is an example of fluidic device 100 discussed further herein with respect to FIGS. 1A-1J. In an embodiment, fluidic device 300 is an example of fluidic device 200 described further herein with respect to FIGS. 2A-2H.

Figure 3B:
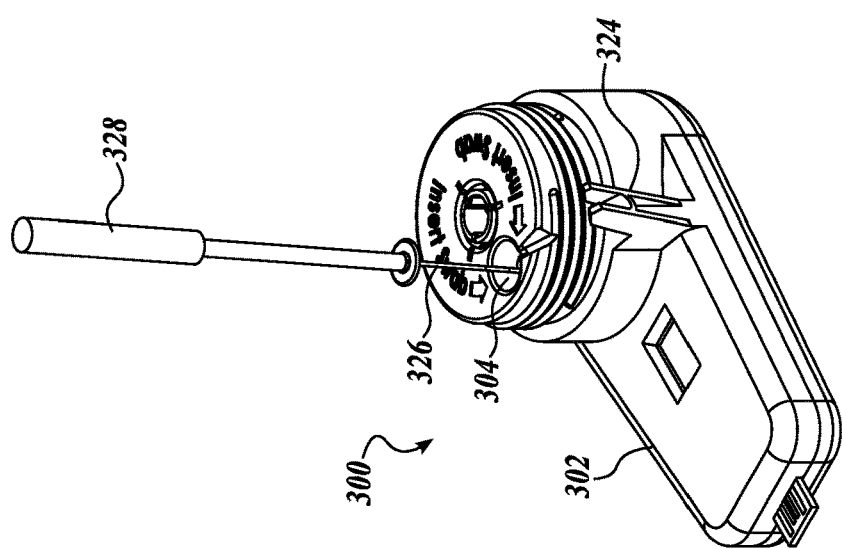
FIG. 3B illustrates a sample collection swab inserted into the fluidic device of FIG. 3A, in accordance with an embodiment of the present disclosure.

FIG. 3B illustrates a sample collection swab inserted into the fluidic device 300 and into the lysis chamber 304.

Figure 3C:
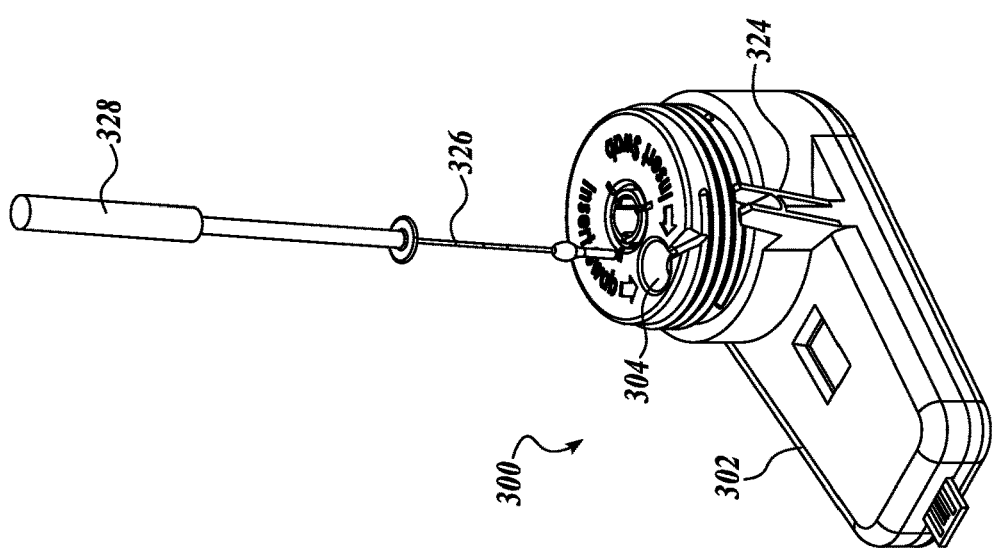
FIG. 3C illustrates coupling the sample collection swab to a bracket of the fluidic device of FIG. 3A, in accordance with an embodiment of the present disclosure.
Figure 3E:
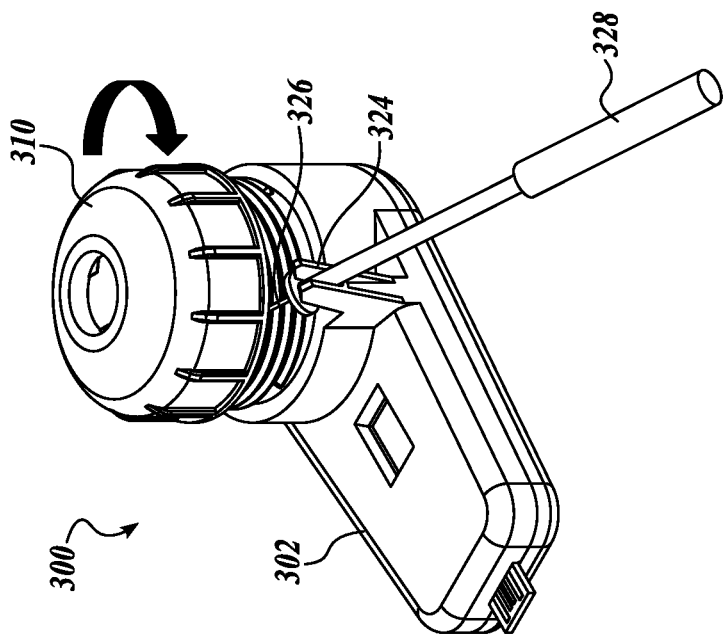
FIGS. 3D and 3E illustrate coupling a cap of the fluidic device of FIG. 3A to a housing of the fluidic device, thereby shearing a stem of the sample collection swab, in accordance with an embodiment of the present disclosure.
Figure 3D:
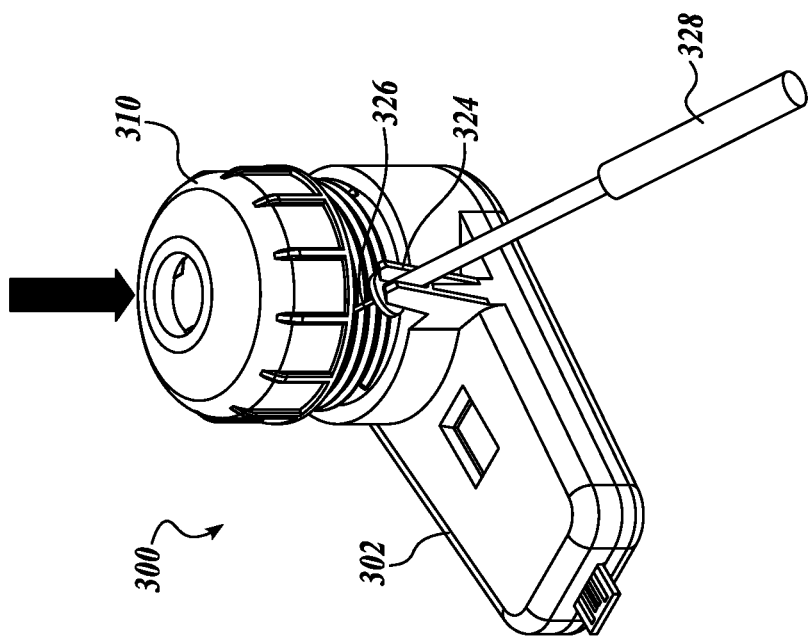

FIG. 3C illustrates coupling the sample collection swab 328 to a bracket 324 of the fluidic device 300, shown here disposed on the housing 302 of the fluidic device 300. FIGS. 3D and 3E illustrate coupling a cap 310 of the fluidic device 300 of FIG. 3A to a housing 302 of the fluidic device 300, thereby shearing a stem 326 of the sample collection swab 328, in accordance with an embodiment of the present disclosure. Once sheared, a portion of the sample collection swab 328 falls into the lysis chamber 304. As discussed further herein with respect to FIGS. 1A-1J, opening the cap 310 places lysis buffer into the lysis chamber 304. As also discussed further herein with respect to FIGS. 1A-1J, closing the cap 310 can also place the lysis buffer and any sample disposed therein in contact with a porous membrane (not shown, see, for example, FIG. 1H) disposed in the housing 302.

In an embodiment, the devices of the present disclosure are suitable to provide a definitive clinically relevant determination of the presence of pathogen RNA (or DNA) in the home, or in other scenarios in which it is not practical to run tests on an expensive and permanent instrument. Home testing for diagnosis in pre-symptomatic and symptomatic individuals is a possible use, with the ability to send data to both healthcare providers, employers, and local, state and national organizations that track cases of infectious diseases. In the case of SARS-CoV-2, a target is identifying pre-symptomatic individuals or those with undifferentiated symptoms. An aim is to allow individuals to self-test at home if they are concerned about their status, or are asked to test by a healthcare provider, employer, or public health official. The ease of use will also allow untrained users to test children or elderly people, and to allow visiting caregivers to provide tests in homes. The low cost and small footprint of these tests would also facilitate testing before airplane flights, at borders, outside of hospitals, before entering worksites or schools, and even in hospitals when large permanent instruments are slow or being used only when fully loaded with samples.

Environmental samples on swabs can be used for immediate monitoring of the effectiveness of decontamination of surfaces in homes, ships, hotels, schools, etc. At least four common home-testing scenarios are contemplated: 1) People purchase a device of the present disclosure to test themselves or household members to determine if someone needs medical treatment. A side-benefit is the automatic transfer of test results to healthcare authorities. 2) An employer purchases a device of the present disclosure for an employee and has it delivered so that the employee can self-test prior to going to a place of work. (Same side benefit). 3) A public health authority pro-actively requests that a person self-test or test a household member to determine if a disease is present and circulating in a region. A test can be mailed overnight or sent by courier to the household at the time of the request. 4) a system with a fixed site needs to screen multiple people to prevent their entry if they are actively infected (e.g., before boarding airplanes, before entering countries, before entering sports stadia, theaters, schools, etc.). An advantage of a device of the present disclosure in addition to an instrumented system is to deal with finite throughput in an instrumented system. In all cases, a major advantage is the rapid time from initiating testing to the provision of data to the patient and the healthcare system.

The devices and systems of the present disclosure have a number of advantageous characteristics and capabilities, a number of which will now be noted.

In an embodiment, the fluidic device detects DNA and/or RNA by an isothermal method (e.g., iSDA).

In an embodiment, the fluidic device accepts swabs for nasal, nasopharyngeal and environmental samples, or saliva with an appropriate applicator.

In an embodiment, the fluidic device has analytical sensitivity no more than one order of magnitude less than commercial laboratory-based RT-PCR tests, clinical sensitivity of >98%, and specificity of 99%.

In an embodiment, the fluidic device has an internal control to validate negative results, such as the capability to identify a human epithelial cell gene to validate sampling.

In an embodiment, the fluidic device is capable of physical multiplexing up to 8 assays. (e.g., for a respiratory panel).

In an embodiment, the fluidic device is coupleable to an external power source, such as to be powered by USB (reusable charger cable or equivalent external battery source).

In an embodiment, the fluidic device is suitable for use within minutes of removal from a foil pouch by untrained personnel, such as with instructions from a smart phone app.

In an embodiment, the fluidic device all buffers are stored in blister packs, such as within the lysis buffer storage chamber, on the fluidic device, and all other reagents are stored dry in the device. In this regard, no bottles or pipettes needed to operate the fluidic device.

In an embodiment, the fluidic device is storable at ambient temperature for up to and/or exceeding 1 year and is still suitable to perform detection reactions.

In an embodiment, the fluidic device needs no laboratory equipment for operation.

In an embodiment, the fluidic device is configured to process sample to provide results in no more than 30 minutes (or less with a strong positive biological sample).

In an embodiment, the fluidic device is configured to produce semi-quantitative results (low, medium, or high levels).

In an embodiment, the fluidic device is configured to provide results only on associated smart phone app.

In an embodiment, the fluidic device is configured to provide real-time fluorescence transmitted via Bluetooth to a user's smart phone, such as wherein analysis of data is performed on phone or in central facility.

In an embodiment, the fluidic device is configured to send results from an app to a user's chosen healthcare providers and/or to regional and national public health systems. In an embodiment, the fluidic device is configured to provide diagnostic and/or therapeutic recommendations to a patient/user through a cell phone app.

Figure 4:
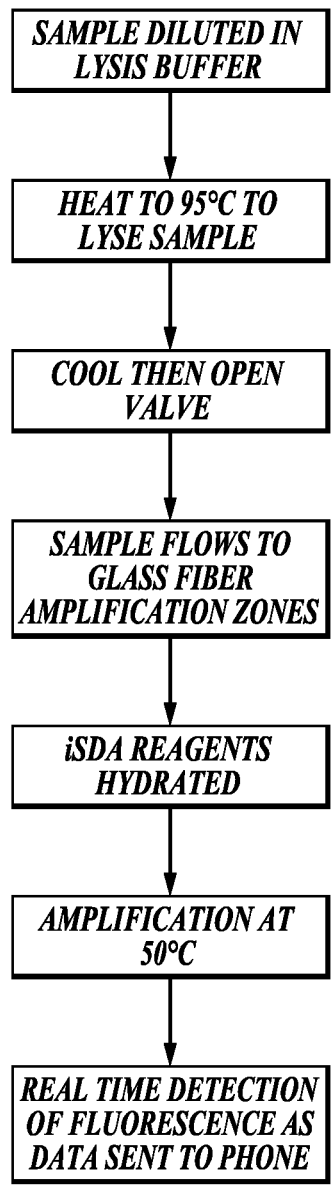
FIG. 4 is a schematic illustration of a method of detection, in accordance with an embodiment of the disclosure.

In an aspect, the present disclosure provides a method of performing an assay to detect an analyte. In this regard, attention is directed to FIG. 4 in which a schematic illustration of a method of detection, in accordance with an embodiment of the disclosure. In an embodiment, the method is a method of operating or using a fluidic device, such as a fluidic device 100 discussed further herein with respect to FIGS. 1A-1J, fluidics device 200 discussed further herein with respect to FIGS. 2A-2H, or fluidics device 300 discussed further herein with respect to FIGS. 3A-3E.

In an embodiment, the assay is a nucleic acid amplification assay configured to amplify an analyte and detect to the analyte or an amplicon thereof. In the illustrated embodiment, the assay is shown to include diluting a sample in lysis buffer, heating the sample to a lysis temperature (shown here as 95 degrees Celsius) to lyse the sample, cool the sample, open a valve to flow the sample to amplification zone(s) of a porous membrane (shown here as a glass fiber amplification pad), hydrating nucleic acid amplification reagents (shown here as iSDA reagents), amplifying the sample at an amplification temperature (shown here as 50 degrees Celsius), and detecting a fluorescence signal, such as in real time, indicating the presence or absence of the analyte or an amplicon thereof.

The order in which some or all of the processes appear in each process should not be deemed limiting. Rather, one of ordinary skill in the art having the benefit of the present disclosure will understand that some of the process blocks may be executed in a variety of orders not illustrated, or even in parallel.

The operations explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit (ASIC) or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

While illustrative embodiments have been illustrated and described, it will be appreciated that various changes can be made therein without departing from the spirit and scope of the invention.

The embodiments of the invention in which an exclusive property or privilege is claimed are defined as follows:

1. A fluidic device comprising:
   a housing defining a lysis chamber shaped to receive a biological sample;
   a lysis buffer storage chamber disposed within the housing and carrying a lysis buffer configured to lyse cells of the biological sample;
   a cap configured to cooperatively couple to the housing;
   a compressor configured to compress the lysis buffer storage chamber and expel the lysis buffer from the lysis buffer storage chamber and into the lysis chamber when the cap is uncoupled from the housing; and
   a porous membrane in selective fluidic communication with the lysis chamber.

2. The fluidic device of claim 1, wherein the compressor comprises:
   a compressor actuator coupled to the cap; and
   a compressor member shaped to couple with the compressor actuator and cooperatively engage with threads defined by the housing to depress the lysis buffer storage chamber when the cap is rotated to uncouple the cap from the housing.

3. The fluidic device of claim 1, further comprising a piercing member shaped and positioned to pierce the lysis buffer storage chamber upon actuation of the compressor to place the lysis buffer storage chamber in fluidic communication with the lysis chamber.

4. The fluidic device of claim 1, wherein the housing further comprises a bracket shaped to couple with a stem of a sample swab, and wherein the cap is shaped to shear the stem as the cap is coupled to the housing when the sample swab is received by the lysis chamber and the stem is coupled to the bracket.

5. The fluidic device of claim 1, further comprising a fluidics printed circuit board configured to receive electrical power from a power source, the fluidics printed circuit board comprising a lysis heater configured to receive electrical power from the power source and positioned to heat the lysis chamber.

6. The fluidic device of claim 5, wherein the fluidics printed circuit board further comprises an amplification heater configured to receive electrical power from the power source and positioned to heat an amplification zone of the porous membrane.

7. The fluidic device of claim 6, wherein the fluidics printed circuit board further comprises a valve heater configured to receive electrical power from the power source and positioned to heat a phase-change valve of the porous membrane configured to selectively place the lysis chamber in fluidic communication with the amplification zone.

8. The fluidic device of claim 1, further comprising an optoelectronics module comprising:
   a light source positioned to illuminate a detection zone of the porous membrane;
   a photodetector positioned to receive fluorescence emitted from the detection zone and generate a fluorescence signal based upon the received fluorescence.

9. The fluidic device of claim 8, wherein the light source and the photodetector are disposed on an optoelectronics printed circuit board in operative communication with the fluidics printed circuit board.

10. The fluidic device of claim 8, wherein the optoelectronics module further comprises:
    a second light source positioned to illuminate a control detection zone of the porous membrane; and
    a second photodetector positioned to receive control fluorescence emitted from the control detection zone of the porous membrane and generate a signal based on the received control fluorescence.

11. The fluidic device of claim 8, wherein the housing further comprises a light control housing shaped and positioned to optically isolate the light source and the photodetector from the second light source and the second photodetector.

12. The fluidic device of claim 1, further comprising a closure sensor configured to generate a closure signal when the cap is cooperatively coupled with the housing.

13. The fluidic device of claim 8, further comprising a transmitter configured to transmit the fluorescence signal.

14. The fluidic device of claim 1, further comprising an identifier uniquely identifying the fluidic device.

15. A diagnostic system comprising:
    a fluidic device comprising:
       a housing defining a lysis chamber shaped to receive a biological sample;
       a lysis buffer storage chamber disposed within the housing and carrying a lysis buffer configured to lyse cells of the biological sample;
       a cap configured to cooperatively coupled to the housing;
       a closure sensor configured to generate a closure signal when the cap is cooperatively coupled with the housing;
       a compressor configured to compress the lysis buffer storage chamber and expel the lysis buffer from the lysis buffer storage chamber and into the lysis chamber when the cap is uncoupled from the housing; and
       a porous membrane in selective fluidic communication with the lysis chamber; and
    a controller in operative communication with the fluidic device including logic that, when executed by the controller, cause the diagnostic system to perform operations including:
       heating the lysis chamber in response to the closure signal.

16. The diagnostic system of claim 15 further comprising a biological sample retrieval device shaped to be received by the lysis chamber when the cap is uncoupled from the housing.

17. The diagnostic system of claim 15, wherein the controller further includes logic that, when executed by the controller, causes the diagnostic system to perform operations including:
    heating a phase-change valve of the porous membrane to place the lysis chamber in fluidic communication with an amplification zone of the porous membrane.

18. The diagnostic system of claim 17, wherein the controller further includes logic that, when executed by the controller, causes the diagnostic system to perform operations including:
    heating the amplification zone.

19. The diagnostic system of claim 15, wherein the fluidic device further comprises an optoelectronics module comprising:
    a light source positioned to illuminate a detection zone of the porous membrane; and
    a photodetector positioned to receive fluorescence emitted from the detection zone and generate a fluorescence signal based upon the received fluorescence,
    wherein the controller further includes logic that, when executed by the controller, causes the diagnostic system to perform operations including:

generating a diagnosis signal based upon the fluorescence signal.

20. The diagnostic system of claim 15, wherein the controller further includes logic that, when executed by the controller, causes the diagnostic system to perform operations including:
transmitting the fluorescence signal.

* * * * *

UNITED STATES PATENT AND TRADEMARK OFFICE
CERTIFICATE OF CORRECTION

Page 1 of 1

PATENT NO. : 12,383,906 B2
APPLICATION NO. : 17/838807
DATED : August 12, 2025
INVENTOR(S) : Paul Yager et al.

It is certified that error appears in the above-identified patent and that said Letters Patent is hereby corrected as shown below:

In the Claims

| Column | Line | |
|---|---|---|
| 12 | 41 | Claim 16, delete "claim 15" and insert -- claim 15, -- |

Signed and Sealed this
Eleventh Day of November, 2025

John A. Squires
*Director of the United States Patent and Trademark Office*